United States Patent [19]
Task
[11] 4,398,822
[45] Aug. 16, 1983

[54] TWO-AXIS ANGULAR DEVIATION MEASUREMENT SYSTEM WITH TARGET IMAGE ROTATING MEANS

[76] Inventor: Harry L. Task, 5513 Snowbank Cir., Dayton, Ohio 45431

[21] Appl. No.: 327,301
[22] Filed: Dec. 3, 1981
[51] Int. Cl.[3] .............. G01N 21/88
[52] U.S. Cl. .............. 356/239; 356/371
[58] Field of Search .............. 356/239, 371, 430, 431; 250/562, 572

[56] References Cited

U.S. PATENT DOCUMENTS

| | | | |
|---|---|---|---|
| 3,025,749 | 3/1962 | Rodman et al. | 356/239 |
| 3,184,735 | 5/1965 | Chapman, Jr. et al. | 343/5 |
| 3,578,869 | 5/1971 | Irland et al. | 356/239 |
| 3,688,235 | 8/1972 | Migeotte | 356/239 |
| 4,249,823 | 2/1981 | Task | 356/128 |
| 4,310,242 | 1/1982 | Genco et al. | 356/239 X |
| 4,377,341 | 3/1983 | Task et al. | 356/239 |

FOREIGN PATENT DOCUMENTS

| | | | |
|---|---|---|---|
| 1308013 | 9/1962 | France | 356/239 |

OTHER PUBLICATIONS

Genco, Louis V. and Task, Harry L., "Aircraft Transparency Optical Quality: New Methods of Measurement", Feb. 1981, Report No. AFAMRL-TR-81-21, pp. 8-19.

*Primary Examiner*—John K. Corbin
*Assistant Examiner*—Matthew W. Koren
*Attorney, Agent, or Firm*—Donald J. Singer; John R. Flanagan

[57] ABSTRACT

An improved system for measuring absolute angular deviation through transparencies, such as aircraft windscreens, uses an incoherent light source and a target configuration in the form of an opaque slide with a transparent "L"-shaped pattern. The positions of images of the legs of the "L" after passing through the transparency are detected at separate times by a single CCD array through rotation of the image of the "L"-shaped pattern ninety degrees by rotation of a Pechan prism about the optical axis of the system. In such manner, horizontal (azimuth) and vertical (elevation) components of angular deviations is measured for each tested point on the transparency, uncontaminated by lateral displacement errors.

4 Claims, 4 Drawing Figures

TWO-AXIS ANGULAR DEVIATION MEASUREMENT SYSTEM WITH TARGET IMAGE ROTATING MEANS

RIGHTS OF THE GOVERNMENT

The invention described herein may be manufactured and used by or for the Government of the United States for all governmental purposes without the payment of any royalty.

CROSS REFERENCE TO RELATED APPLICATION

Reference is hereby made to the following co-pending U.S. application disclosing subject matter upon which the present invention constitutes an improvement: "An Improved System for Measuring Angular Deviation in a Transparency," by Harry L. Task et al, U.S. Ser. No. 242,816, filed Mar. 11, 1981 now U.S. Pat. No. 4,377,341.

BACKGROUND OF THE INVENTION

1. Field of the Invention

The present invention broadly relates to the measurement of angular deviation in a transparency and, more particularly, is concerned with an improved two-axis angular deviation measurement system utilizing means for rotating a target image to change between measuring horizontal and vertical angular deviations.

2. Description of the Prior Art

As a general rule, optically transparent, asymmetrically contoured bodies have been difficult to quantitatively evaluate and compare on the basis of their optical characteristics. A prime example of a structural element formed of a transparent medium in which optical quality is critical, yet difficult to quantitatively evaluate, is the canopy or windscreen of aircraft having complex curvilinear contours.

Distortion is one of the optical quality parameters that has been identified for characterizing transparencies, such as aircraft windscreens. Distortion is the nonlinear mapping of object points to image space due to the optical effects of the transparency. Such effects may be due to either optical index variations in the transparency or to the opposite faces of the transparency being non-parallel.

In a more technical vein, distortion has been defined as the rate of change of angular deviation across the transparency. Angular deviation is defined as the angular deflection or change of direction of a light ray as it passes through the transparency. Theoretically, the distortion in any transparency may be determined by mapping at a plurality of locations on the transparency the angular deviation of light rays as they are transmitted from the object through the transparency to the observer.

While several methods of measuring angular deviation have been employed in the past, none have proven to be as satisfactory as the system disclosed in the above cross-reference application. This system uses incoherent light and a unique target configuration, and achieves excellent accuracy and repeatability. The unique target configuration is an opaque slide with a transparent pattern in the shape of an "L". Images of the legs of the "L" are used to detect and measure the azimuth (horizontal) and elevation (vertical) components of angular deviation for each tested point on the windscreen.

After the image of the transversely-aligned segments or legs of the L are projected through the test region containing the transparent windscreen, the image is reflected and transmitted by a beam splitter into first and second channels having first and second optical axes. First and second linear detector arrays are located respectively along the first and second optical axes for facilitating detection and measurement of azimuth and elevation components of angular deviation for each tested point on the aircraft windscreen positioned in the test region. The first detector array is located across one of the linear segments or legs of the L, whereas the second detector array is located across the other linear segment or leg of the L. The first and second detector arrays detect lateral shifts in the position of the respective images of the transparent pattern linear segments which correspond to azimuth (horizontal) and elevation (vertical) components of angular deviation for a particular point on the transparency, the lateral shifts occurring if at all, when the transparency is inserted into the test region.

While this system of the cross-referenced application accomplishes its intended purpose in an uncomplicated and efficient manner, it requires rather expensive electro-optical components, such as the CCD components which serve as the arrays. Therefore, a need exists for simplifying the design and reducing the cost of the system without eliminating any of the advantages fostered by the system in carrying out quantitative measurement of angular deviation in transparencies.

SUMMARY OF THE INVENTION

The present invention provides an improvement of the angular deviation measurement system of the above cross-referenced application, which is designed so as to substantially satisfy the aforementioned need. The improved measurement system employs only one linear detector array in conjunction with an image rotator to obtain two-dimensional angular deviation data. By rotating the image rotator about the optical axis of the system, the system switches between vertical (elevation) and horizontal (azimuth) angular deviation measurement by the single linear detector array. Consequently, like its predecessor, the improved system measures accurately both horizontal and vertical angular deviation of a ray of light traversing a transparent medium, but, unlike it, requires only one detector array and associated electronics.

Accordingly, the present invention provides an improved system for measuring angular deviation in a transparency which includes an incoherent light target projection means coupled with a receiver lens means, but with only one linear detector array at the focal plane of the receiver lens means. An image rotating means, such as a Pechan prism, is located between the detector array and the receiver lens means and is rotatable about the optical axis for rotating an "L"-shaped target image to change or switch between measuring horizontal and vertical angular deviations at the detector array. The rotation of the target image causes a different one of the images of the transversely-aligned legs of the "L"-shaped target to intersect with the single linear array. The lateral shift in the position of the image of one leg along the array is caused by vertical angular deviation, while lateral shift in the position of the image of the other leg along the array is caused by horizontal angular deviation, in the region of the transparency under test.

DETAILED DESCRIPTION OF THE INVENTION

Figure 1:
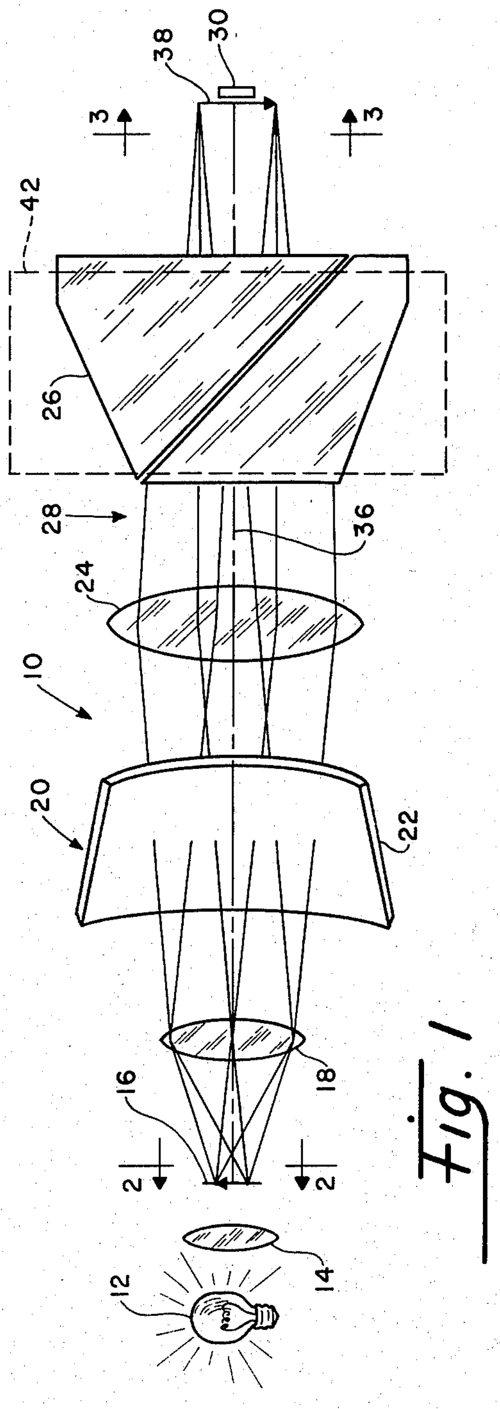
FIG. 1 is a side elevational view in schematical form of the improved angular deviation measurement system of the present invention.

Referring now to the drawings, and more particularly to FIG. 1, there is shown schematically the preferred embodiment of the improved angular deviation measurement system of the present invention, being generally designated 10. The system 10 includes a source of incoherent light 12, such as an incandescent lamp, which radiates light which is collected by a condensing lens 14 to illuminate a target slide 16. A projection lens 18 of the system 10 located one focal length from the target slide 16 on the side thereof opposite from the condensing lens 14, collimates the image of the target slide 16 and projects it through a test region, generally designated 20. A transparency 22 undergoing test, such as an aircraft windscreen, is shown inserted into the region 20.

The portion of the improved system 10 just described is positioned to the left of the transparency 22 such that the projection lens 18 is approximately at the observer (or design eye) position for the transparency 22 under test. The remainder of the improved system, the receiver portion, is located on the other (right) side of the transparency 22.

In order to compensate for lateral displacement of the image and thus eliminate an error source due to its passage at an oblique angle through the transparency 22, a collection or receiving lens 24 is positioned to the right of the transparency 22 for receiving the image projected through the transparency 22 from the projection lens 18. The parts of the system 10 described up to this point, such being those parts to the left of the transparency 22 and the receiving lens 24 to the right of the transparency, are all found in the predecessor system of the above cross-referenced application.

The improvement provided by the present invention is embodied primarily by an image rotator 26, preferably in the form of a Pechan prism. The image rotator 26 is disposed along a single channel 28 defined by the receiving lens 24 and intercepts light forming the image of the target slide 16 which is focused by the receiving lens 24 one focal length to its right at a location beyond a linear detector device 30 also positioned in the channel 28. A particular advantage of using a Pechan prism as the image rotator 26 is that it folds the path of the light, thereby reducing the distance to the focal plane of the receiving lens 24, such that the focal plane is positioned at the location of the detector device 30, as seen in FIG. 1, instead of to the right thereof. As a consequence, the length of space required to contain the system 10 is reduced.

Figure 2:
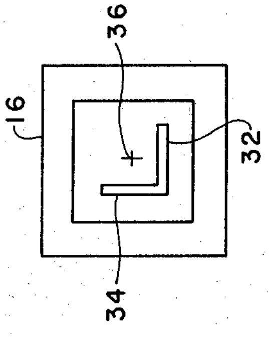
FIG. 2 is an enlarged view as seen along line 2—2 of FIG. 1 of the target slide used in the improved measurement system.

The target slide 16 is identical to the one used in the predecessor system. It is substantially opaque with a transparent pattern formed therein by a pair of transversely-aligned linear segments 32, 34, as seen in FIG. 2. In the illustrated embodiment of the slide 16, the transparent pattern is in the form of the letter "L" in which the linear segments 32, 34 are defined by the two legs of the "L" and are orthogonally aligned with one another. The dimensions and location of the "L"-shaped pattern are not particularly critical; however, the width of the legs of the "L" must be uniform to reduce error. Each of the linear segments or legs 32, 34 of the "L"-shaped pattern is offset from an optical axis 36 of the system 10.

Figure 3:
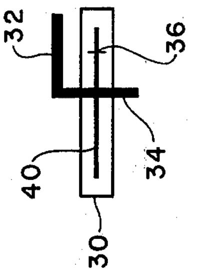
FIG. 3 is a schematical representation as seen along line 3—3 of FIG. 1 of the intersection of the image of the "L"-shaped transparent pattern of the opaque target slide with the single linear detector array.
Figure 4:
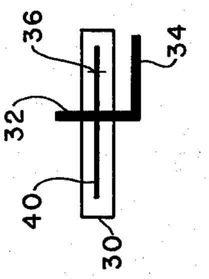
FIG. 4 is a schematical representation similar to FIG. 3, but illustrating the intersection of the image of the "L"-shaped transparent pattern after it has been rotated ninety degrees in a counterclockwise direction from its orientation in FIG. 3.

In contrast to the predecessor system, the improved system 10 uses only a single detector device 30 which, as before, may take the form of a charge coupled device (CCD) linear (or one dimensional) array. As seen in FIG. 1, the device 30 is disposed in a horizontal plane. The target slide 16 and detector device 30 are so located relative to the optical axis 36 of the improved system 10 that one leg 34 of the image of the "L"-shaped pattern, produced at the focal plane 38 of the receiver portion of the system and coincident with the linear light-receiving face 40 of the CCD array 30, intersects or crosses the face 40. It will be noted in both FIGS. 3 and 4 that the CCD array 30 is not centered on the optical axis 36; instead, its center is preferably offset therefrom by a distance generally equal to the distance between the optical axis 36 and the non-intersecting one of the legs 32, 34 of the "L". The location of the intersection is detected by the detector array 30 and its associated electronics (not shown). The positional change or lateral shift of the intersection between when the transparency 22 is presented in the test region 20 and when it is not is mathematically related to the angular deviation of the transparency 22 at the particular point being measured. Only a few CCD elements of the 512 elements of the linear array 30 receive light forming the respective one of the segments or legs 32, 34 and are activated. The array 30 is sampled and a measurement value obtained by the use of an electrical circuit, such as the one disclosed by Kenneth L. Smith in patent application Ser. No. 118,007 filed Feb. 4, 1981, now U.S. Pat. No. 4,309,106, the disclosure of which is incorporated by reference.

The image rotator or Pechan prism 26, which was briefly discussed above, is mounted for rotating about the optical axis 36 by any suitable means, such as within a housing or casing 42 shown in dashed outline form in FIG. 1. The prism 26 may be rotated manually or by some suitable automatic means such as a solenoid. In the angular rotational position of the prism 26 in FIG. 1, the one leg 34 crosses the light-receiving face 40 of the detector array in the orientation depicted in FIG. 3 and the system 10 is set to measure horizontal angular deviation of light through the transparency 22. By rotating the prism 26 through forty-five degrees counterclockwise, the target image is rotated through ninety degrees in a counterclockwise direction to the position shown in FIG. 4 in which the image of the other target leg 32 crosses the light-receiving face 40 of the array 30. The system 10 now measures vertical angular deviation of light through the transparency 22. It is readily seen that the employment of the prism 26 eliminates the need for the beam splitter and second linear array along with its associated drive and display electronics in the predecessor system.

It is thought that the invention and many of its attendant advantages will be understood from the foregoing description and it will be apparent that various changes may be made in the form, construction and arrangement of the parts thereof described without departing from the spirit and scope of the invention or sacrificing all of its material advantages, the form hereinbefore described being merely a preferred or exemplary embodiment thereof.

Having thus described the invention, what is claimed is:

1. In a system for measuring angular deviation in a transparency, said system having a predetermined optical axis and including an opaque object having a transparent pattern formed therein by a pair of transversely-aligned segments, an incoherent light source for illuminating said object, and means for projecting an image of said transversely-aligned segments through a test region of space, the improvement which comprises:

(a) means for receiving said projected image and for transmitting it, after having removed any effects of lateral displacement of the image, into a predetermined channel;

(b) a linear detector array aligned with said optical axis and positioned in said predetermined channel for detecting a lateral shift in the position of the image of one of said transparent pattern segments due to angular deviation for a particular point on said transparency, the lateral shift occurring, if at all, when the transparency is inserted into the test area; and (c) said receiving means including means actuatable for rotating the image of said transparent pattern segments about said optical axis to dispose the image relative to said array such that any lateral shifts in the position of, first, the image of one and, then, the image of the other of said segments are detected successively by said array.

2. The angular deviation measuring system as recited in claim 1, wherein said linear detector array is located in a focal plane of the image in said channel such that, first, the image of one and, then, the image of the other of said segments of said transparent pattern are disposed across said detector array by activation of said image rotating means.

3. The angular deviation measuring system as recited in claim 1 or 2, wherein said image rotating means is comprised by a rotatable Pechan prism.

4. In an improved system for measuring angular deviation in a transparency, such as the windscreen of an aircraft, the combination comprising:

(a) a target in the form of an opaque slide with a transparent "L"-shaped pattern;

(b) an incoherent light source for illuminating said target;

(c) means for forming and transmitting an image of said "L"-shaped pattern through said transparency and free of the effects of lateral displacement into a predetermined channel, said means defining a predetermined optical axis;

(d) a linear CCD (charge coupled device) array aligned with said optical axis and located in said channel for detecting the position of the image of said "L"-shaped pattern, one leg at a time, after being transmitted through said transparency and into said channel and thereby facilitating measurement of azimuth and elevation components of angular deviation in said transparency; and (e) a Pechan prism aligned in said channel between said linear CCD array and said forming and transmitting means and being rotatable about said optical axis for rotating the image of said "L"-shaped pattern such that, first, the image of one and, then, the image of the other of the legs of said "L"-shaped pattern are disposed across said linear CCD array.

* * * * *